US010010573B2

(12) United States Patent
Duan et al.

(10) Patent No.: US 10,010,573 B2
(45) Date of Patent: Jul. 3, 2018

(54) ENGINEERED RICE HAVING ALCOHOLISM RELIEF AND LIVER PROTECTION FUNCTION, AND PREPARATION METHOD THEREOF

(71) Applicants: CHINA NATIONAL RESEARCH INSTITUTE OF FOOD AND FERMENTATION INDUSTRIES CO., LTD., Beijing (CN); PERFECT (CHINA) CO., LTD., Guangdong (CN)

(72) Inventors: Shenglin Duan, Beijing (CN); Muyi Cai, Beijing (CN); Zhe Dong, Beijing (CN); Yanqiao Liu, Beijing (CN); Xue Wang, Beijing (CN); Shiwei Liu, Beijing (CN); Jie Liu, Beijing (CN); Ruilian Hu, Guangdong (CN); Zian Li, Guangdong (CN)

(73) Assignees: China National Research Institute of Food and Fermentation Industries Co., Ltd., Beijing (CN); Perfect (China) Co., Ltd., Guangdong (CN)

( * ) Notice: Subject to any disclaimer, the term of this patent is extended or adjusted under 35 U.S.C. 154(b) by 643 days.

(21) Appl. No.: 14/529,286

(22) Filed: Oct. 31, 2014

(65) Prior Publication Data
US 2015/0118336 A1 Apr. 30, 2015

Related U.S. Application Data

(63) Continuation of application No. PCT/CN2013/074792, filed on Apr. 26, 2013.

(30) Foreign Application Priority Data

May 2, 2012 (CN) .......................... 2012 1 0131260

(51) Int. Cl.
| | |
|---|---|
| A61K 36/899 | (2006.01) |
| A61K 36/39 | (2006.01) |
| A61K 36/488 | (2006.01) |
| A61K 36/734 | (2006.01) |
| A61K 38/16 | (2006.01) |
| A61K 36/48 | (2006.01) |
| A23L 7/143 | (2016.01) |
| A23L 33/105 | (2016.01) |
| A23L 33/17 | (2016.01) |
| A23L 33/18 | (2016.01) |
| A23L 33/185 | (2016.01) |

(52) U.S. Cl.
CPC ............ *A61K 36/899* (2013.01); *A23L 7/143* (2016.08); *A23L 33/105* (2016.08); *A23L 33/17* (2016.08); *A23L 33/18* (2016.08); *A23L 33/185* (2016.08); *A61K 36/39* (2013.01); *A61K 36/48* (2013.01); *A61K 36/488* (2013.01); *A61K 36/734* (2013.01); *A61K 38/168* (2013.01); *A23V 2002/00* (2013.01); *A61K 2236/00* (2013.01)

(58) Field of Classification Search
None
See application file for complete search history.

(56) References Cited

U.S. PATENT DOCUMENTS

2003/0138531 A1* 7/2003 Saito .................. A23L 2/39
426/249

FOREIGN PATENT DOCUMENTS

| CN | 101703592 A | * 5/2010 | |
|---|---|---|---|
| CN | 101731630 | 6/2010 | ............. A23L 1/305 |
| CN | 102106520 | 6/2011 | ............. A23L 1/216 |
| CN | 102318857 | 1/2012 | ............... A23L 2/38 |
| CN | 102648751 | 8/2012 | ............... A23L 1/10 |

OTHER PUBLICATIONS

International Search Report issued in a corresponding foreign application, pp. 1-5 (dated Nov. 7, 2013).
Zhang, Fu Sheng, "Study on the processing technology of nutritional engineering cereal" A Dissertation for the Master's Degree of SWU, pp. 1-67 (2008).

* cited by examiner

*Primary Examiner* — Terry A McKelvey
*Assistant Examiner* — Catheryne Chen
(74) *Attorney, Agent, or Firm* — J. Peter Paredes; David G. Rosenbaum; Rosenbaum IP, P.C.

(57) ABSTRACT

The present invention relates to a functional engineered rice having alcoholism relief and liver protection functions for those drinking alcohol over an extended period of time or drinking alcohol excessively, and preparation method thereof. The engineered rice comprises six starting materials: coarse rice powder, isolated soy protein, kudzu root extract, corn oligopeptide, purple sweet potato powder, and hawthorn extract, and is prepared by: premixing the starting materials; employing a double screw extruder to conduct texturized processing and forming under high temperature and high pressure; and then drying, dedusting and packaging.

5 Claims, No Drawings

ENGINEERED RICE HAVING ALCOHOLISM RELIEF AND LIVER PROTECTION FUNCTION, AND PREPARATION METHOD THEREOF

CROSS-REFERENCE TO RELATED APPLICATIONS

The present application claims priority from and is a continuation from PCT Application No. PCT/CN2013/074792, filed Apr. 26, 2013, which claims priority from Chinese Patent Application No. CN 201210131260.3, filed May 2, 2012, each of which is incorporated by reference in its entirety herein.

TECHNICAL FIELD OF THE INVENTION

The present invention relates to an engineered rice having alcoholism relief and liver protection functions and the preparation method thereof.

BACKGROUND OF THE INVENTION

Liver is an organ having a predominant function of metabolism in the body, and not only plays a role in deoxidation, storage of glycogen and synthesis of secretory proteins etc. in vivo, but also has a function of producing bile in the digestive system. Hepatopathy is a lesion occurring in the liver, which may be induced by a variety of causes. Hepatopathy is always one of killers that would be harmful to human health. So far, once the patients suffer from liver cancer or cirrhosis, it is difficult to save them even using the most advanced medical means. The etiology of hepatopathy is complicated. According to the etiology and some clinical manifestations of hepatopathy, it can be divided into the following: viral hepatitis, such as hepatitis A, hepatitis B, etc.; alcoholic liver disease, such as fatty liver, alcoholic hepatitis, liver fibrosis, cirrhosis and hepatocellular carcinoma, etc. 90% to 95% of human intake of ethanol is metabolized by the liver. Upon entering into hepatic cells, ethanol is oxidized by liver alcohol dehydrogenase, hydrogen peroxide decomposition enzyme and liver microsomal alcohol oxidase to form acetaldehyde. Acetaldehyde has significant toxic and side effects on hepatic cells to hinder metabolism, leading to the degeneration and necrosis of hepatic cells. Alcohol consumption and frequency of drinking determine the extent of liver damage. It is estimated that there are around 15 million to 20 million alcoholics all over the world, 10%-20% of which (1.5 million to 4 million) suffer from different degree of alcoholic liver disease. The early-stage patient with alcoholic liver disease may show no symptoms at all, but at this time, the liver tissue has undergone pathologic change. With the increasing development of social life and the accelerated pace of life, alcoholic liver disease is also becoming younger in average age and more popular. A lot of people around are talking about fatty liver, known as an "illness of affluence", which has been gradually becoming more common and poses serious threat to people's health. It becomes the second largest hepatopathy after viral hepatitis and has been recognized as a common cause of concealed cirrhosis. Meanwhile, fatty liver can aggravate the primary pathological changes and easily induce or aggravate diseases such as hypertension, coronary heart disease, atherosclerosis, even lead to occurrence of liver cancer. Unhealthy dietary habits are often the chief culprit leading to fatty liver, thus people should pay more attention to their diet in daily life.

In recent years, hangover drinks and foods, such as hangover pills, hangover sugar, chewing tablets and oral liquid have been successfully developed. However, the majority of such products do not show obvious effect, and they are of high cost and expensive, belonging to high-end consumer goods, thus there are certain market limitations. After several years of in-depth study, a hangover product, i.e. corn oligopeptide food, stands out due to the fact that it is of lower cost and healthier. Ethanol in the liver of human body is catabolized by ethanol dehydrogenase and acetaldehyde dehydrogenase, and more than 90% of ethanol is absorbed by the liver. Corn oligopeptide can promote biochemical reactions in the metabolic pathway of alcohol dehydrogenase in vivo, and thereby reducing the concentration of ethanol in the blood. Such new hangover agent is prepared by hydrolyzing corn germ meal by alkaline protease, filtrating, and formulating with suitable excipients such as amino acids and vitamins, and can exert effectively dealcoholic and hepatoprotective functions. A study has shown that, after spontaneously hypertensive rats with stroke tendency were fed with corn peptide and ethanol successively, by comparison with the control, it was found that the contents of ethanol and its oxidative product acetaldehyde in the blood were significantly reduced. The human trials gave the same result that the content of ethanol in the blood was relatively significantly reduced, while the contents of Ala, Leu, Pro in the plasma had a substantial increase and maintained a high level for 2 hours. Corn peptide plays a positive role on alcohol metabolism by increasing the concentration of alanine and leucine in the blood and producing stable $NAD^+$.

SUMMARY OF THE INVENTION

Provided herein are systems, methods and compositions for an engineered rice having alcoholism relief and liver protection functions, comprising in the materials thereof comprise the following components by parts of weight: about 70-85% of coarse rice powder, about 5-25% of isolated soy protein, about 0.01-5% kudzu root extract, about 0.5-5% of corn oligopeptide, about 2-10% of purple sweet potato powder, about 1-9% of hawthorn extract.

A method for preparing the engineered rice having alcoholism relief and liver protection functions is disclosed, comprising the steps of: a. weighing each component according to the required amount of formulation, mixing uniformly coarse rice powder, isolated soy protein, kudzu root extract, corn oligopeptide, purple sweet potato powder with hawthorn extract to obtain the staring material A for use; b. employing a double screw extruder to conduct extrusion forming to obtain the product B, wherein the control parameters of production process are: feed rate of 200-300 kg/h, extrusion temperature of 80-190° C., moisture content of 10-34% and peeling speed of 400-650 rpm; c. processing the product B under water-controlling by cold-blast air followed by the steps of drying, dedusting and packaging to obtain the final product C.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

An object of the invention is to develop and produce a functional engineered rice having dealcoholic and hepatoprotective functions, which can enhance the metabolism of ethanol inside the body, reduces liver damage and restore liver vitality.

Another object of the invention is to develop a method for producing a functional engineered rice having dealcoholic and hepatoprotective functions which is capable of enhancing the metabolism of ethanol inside the body, reducing liver damage and restoring liver vitality.

The objects of the invention are achieved by the following technical solutions:

An engineered rice having alcoholism relief and liver protection functions, the starting materials thereof comprising the following components by parts of weight:

| unit of measurement: | kg |
|---|---|
| coarse rice powder | about 70-85 |
| isolated soy protein | about 5-25 |
| kudzu root extract | about 0.01-5 |
| corn oligopeptide | about 0.5-5 |
| purple sweet potato powder | about 2-10 |
| hawthorn extract | about 1-9 |

In the present invention, the coarse rice powder is prepared by smashing coarse rice that is produced after process of rice. Coarse rice after shelling still retains some external tissues, such as cortex, aleurone layer and germ. Such external tissues are rich in nutrients, and contain more vitamins, minerals and dietary fiber than rice. Coarse rice bran and germ portions are rich in vitamin B and vitamin E, which can improve immune function of human body and promote blood circulation. In addition, coarse rice has high contents of trace elements, such as potassium, magnesium, zinc, iron, manganese, and is useful to prevent cardiovascular disease and anemia. Coarse rice has the effects of cracking and decomposition of radioactive substances such as pesticides, and thereby effectively preventing the absorption of harmful substances in the body, and achieving the hepatoprotective effect.

The isolated soy protein has a protein content of more than 90% and nearly 20 kinds of amino acids, and contains essential amino acids for the human body. Isolated soy protein is rich in nutrition and free of cholesterol. In addition, the isolated soy protein is free of trypsin inhibitor, an original nutrition inhibition factor in soybean, and does not lead to discomfort reactions such as indigestion and flatulence and the like.

The kudzu root extract is originated from dried root of leguminous plants of *Pueraria*. In addition to the nutrients such as the carbohydrates, essential amino acids for human body and mineral elements, Lobed kudzuvine root contains isoflavone compounds and a small quantity of flavonoids. In lobed kudzuvine root, the daidzein, daudzin and *pueraria* are main active ingredients, especially the content of *pueraria* is the highest. *Pueraria* has the effects of expanding blood vessels, improving blood circulation; reducing myocardial oxygen consumption, inhibiting cancer cell; increasing coronary blood flow and regulating blood microcirculation. Kudzu root extract can improve regeneration of liver cells, restore normal liver function, promoting bile secretion, prevent the accumulation of fat in the liver, promoting metabolism, enhance liver detoxification function and prevent the damage of alcohol on the liver.

The corn oligopeptide is a small molecule polypeptide substance obtained from the protein extracted from natural food corn by directional restriction enzyme digestion and special small peptide separation technology. It contains various essential amino acids for human body to provide amino acid and peptidergic nutrition, and has the effect of inhibiting angiotensin converting enzyme, thereby reducing blood pressure. Others small peptides have the functions of antifatigue, liver protection and improvement of immunity of the body. Corn peptide can inhibit absorption of alcohol by stomach, increase the activity of alcohol dehydrogenase and aldehyde dehydrogenase and promote the metabolism and excretion of alcohol in the body.

The purple sweet potato powder: the purple sweet potato contains abundant proteins, 18 types of amino acids easily digested and absorbed by human body, 8 vitamins such as vitamin C, B and A and more than 10 natural minerals such as phosphorus and iron, wherein, iron and selenium have abundant contents. It is also rich in anthocyanin. Anthocyanin has the effects of preventing and treating over 100 diseases, and is currently regarded as the most direct, effective and safe radical scavenger found in the scientific community for prevention and treatment of diseases and health maintenance of human beings. Its ability to scavenge radicals is 19 times greater than vitamin C and 49 times greater than vitamin E, and it has the functions of preventing hypertension and alleviating liver dysfunction as well as good anti-cancer function. Animal experiments show that anthocyanins can significantly inhibit the increasement of glutamic-oxaloacetic transaminase (GOT) and glutamic acid-pyruvic acid transaminase (GPT) in serum of mice with acute liver injury, and have some inhibitory effects on an increase in thiobarbituric acid (TBA) reactants and oxidized lipoprotein in serum and liver.

The hawthorn extract is extracted from desiccative ripe fruit of hawthorn, also known as large-fruited Chinese hawthorn, which is a plant of the genus *Crataegus*, Rosaceae. Hawthorn is sour in taste, sweet and slightly gentle in nature, enters into spleen stomach and liver. Hawthorn has the effects of increasing myocardial contraction force, increasing cardiac output and slowing heart rate. The total flavonoids have the effects of increasing coronary blood flow, reducing myocardial oxygen consumption and myocardial oxygen utilization, as well as certain effect of increased myocardial nutritional blood flow, and prevent or alleviate myocardial ischemia or necrosis caused by isopropyl adrenaline. While Hawthorn enters into stomach, it can enhance the effect of enzyme, thereby promoting the digestion of meat and helping the conversion of cholesterol. Hawthorn contains ursolic acid that can reduce deposition of animal fat on blood vessel walls and thereby digesting the food and removing the fat, thus it is a good hepatoprotective food.

The technological process of production of the functional engineered rice having dealcoholic and hepatoprotective functions according to the invention is described as below: weighing each component according to the required amount of formulation, mixing uniformly coarse rice powder, isolated soy protein, kudzu root extract, corn oligopeptide, purple sweet potato powder with hawthorn extract to obtain the staring material A for use; employing a double screw extruder to conduct texturized processing and forming under high temperature and high pressure to obtain the product B, wherein the control parameters of production process are: feed rate of 200-300 kg/h, extrusion temperature of 80-190° C., moisture content of 10-34% and peeling speed of 400-650 rpm; processing the product B under water-controlling by cold-blast air followed by the further steps of drying, dedusting and packaging to obtain the final product C.

The main raw material of the invention is coarse cereals which is organic, pure and nutritionally balanced and can ensure nutritional requirement of eaters. The additional functional components are mainly natural raw materials or the extract of natural raw materials, which are safe, reliable and have significant efficacy. At first, the invention preferably selects coarse rice powder and isolated soy protein as basic materials, thereby not only providing essential energy substances such as carbohydrates and proteins to ensure basic intake of energy, but also providing a plurality of nutritional factors such as vitamins and minerals, some of which are the functional components beneficial to dealcoholic and hepatoprotective purposes and can contribute to advantageous effect of the present invention. More importantly, the key and innovation of the invention is the combination of kudzu root extract, corn oligopeptide, purple sweet potato powder and hawthorn extract can inhibit absorption of alcohol by stomach, increase the activities of alcohol dehydrogenase and aldehyde dehydrogenase in the body, enhancing detoxification of liver, promote the metabolism and excretion of alcohol in the body, as well as improve regeneration of liver cells, restore normal liver function, promote bile secretion, promote digestion and prevent the accumulation of fat in the liver, and therefore has dealcoholic and hepatoprotective effects. The invention further comprises the forming process of product, wherein the technical parameters such as feed rate, extrusion temperature, moisture content of material and peeling speed are optimized. Finally, the invention produces a functional engineered rice having dealcoholic and hepatoprotective functions which is capable of enhancing the metabolism of ethanol inside the body, reducing liver damage and restoring liver vitality.

The following examples are intended to illustrate the invention, but not to limit the scope of the invention.

In the examples, the double screw extruder is purchased from Wenger Manufacturing Inc., USA; and the drying system is purchased from Wenger Manufacturing Inc., USA.

The isolated soy protein is purchased from Shangdong Dezhou Gushen Biological Technology Group Co., Ltd., and has a protein content (dry basis) of ≥90% and a nitrogen soluble index (NSI) of ≥85;

The kudzu root extract is purchased from Xi'an Rongsheng Biotechnology Co., Ltd., and has a puerarin content of ≥40% (measured by HPLC)

The corn oligopeptide purchased from Beijing Zhongshihaishi biotechnology Co., Ltd., and has total protein content of ≥80%.

The purple sweet potato powder, known as purple potato powder, is purchased from Tianjin Zhenruguo Food Industry Co., Ltd., and has a starch content of ≥55% and The hawthorn extract is purchased from Jiangyin Tianjiang Pharmaceutical Co., Ltd., which is brown or tan fine powder and has a hawthorn flavone content of 9% (measured by UV).

The methods for determination of the product composition are shown in Table 1.

TABLE 1

| Item | Method |
|---|---|
| | The methods for determination of the composition |
| Protein | GB/T 5511-2008 Cereals and pulses - Determination of the nitrogen content and calculation of the crude protein content |
| Total sugar | GB/T 5009.8-2008 Determination of saccharose in foods |
| Fat | GB/T 5009.6-2003 Determination of fat in foods |
| Moisture | GB 5009.3-2010 National food safety standard; Determination of moisture in foods |
| Iron, magnesium, manganese | GB/T 5009.90-2003 Determination of iron, magnesium and manganese in foods |
| Aluminum | GB/T 5009.182-2003 Determination of aluminum in flour products |
| Zinc | GB 5009.14-2003 Determination of Zinc in foods |
| Ash | GB/T 22427.1-2008 Determination of ash in starches |
| Dietary fiber | GB/T 5009.88-2008 Determination of dietary fiber in foods |
| Total Carbohydrate | Subtraction calculation (100 – total nitrogen – fat-- moisture-ash and dietary fiber |
| Total flavone | Technical Standards for Testing & Assessment of Health Food, 2003 edition, |
| Lovastatin | Technical Standards for Testing & Assessment of Health Food, 2003 edition, |
| Procyanidine | Technical Standards for Testing & Assessment of Health Food, 2003 edition, |
| Aflatoxin B1 | GB 2763-2005 Maximum residual limits for pesticides in foods |
| Benzex | GB 2763-2005 Maximum residual limits for pesticides in foods |
| DDT | GB 2763-2005 Maximum residual limits for pesticides in foods |
| Heptachlor | GB 2763-2005 Maximum residual limits for pesticides in foods |
| DDVP | GB 2763-2005 Maximum residual limits for pesticides in foods |
| Methamidophos | GB 2763-2005 Maximum residual limits for pesticides in foods |

The functional engineered rice having dealcoholic and liver protection functions and the preparation method thereof according to the present invention are illustrated in details by the specific examples below.

Example 1

| Unit of measurement: | kg |
|---|---|
| Coarse rice powder | 70 |

-continued

| Isolated soy protein | 25 |
| Kudzu root extract | 1 |
| Corn oligopeptide | 1 |
| Purple sweet potato powder | 2 |
| Hawthorn extract | 1 |

The particular preparation method of the example comprises the steps of:

a. weighing each component according to the required amount of formulation, mixing uniformly coarse rice powder, isolated soy protein, kudzu root extract, corn oligopeptide, purple sweet potato powder with hawthorn extract to obtain the staring material A for use;

b. employing a double screw extruder to conduct texturized forming on the staring material A under high temperature and high pressure to obtain the product B, wherein the control parameters of production process include: feed rate of 200 kg/h, extrusion temperature of 80° C., water addition to moisture content of 10% and peeling speed of 400 rpm;

c. processing the product B by drying at a low temperature of 70° C. followed by the further steps of drying at 100° C., removing impurities by shaker and packaging, etc. to obtain the final product C, i.e. the engineered rice having dealcoholic and hepatoprotective functions (hereinafter referred to as hepatoprotective rice).

The shape and size of the product particles are similar to those of ordinary indica, the color is dark red, and for per 100 kg of raw materials 99 kg of products are produced. The composition test of the hepatoprotective rice is shown in Table 2.

Edible Method:

1. Consumption Alone hepatoprotective rice:water=1:0.7, after the water boils putting them into steam bowl, and steaming for 15 min; or, hepatoprotective rice:water=1:1.4, putting them into a rice cooker and cooking in ultra-fast mode for 20 min.

2. Consumption in a Mixture

Ordinary rice:hepatoprotective rice:water=3:1:4, after the water boils putting them into steam bowl, and steaming for 40 min; or, Ordinary rice:hepatoprotective rice:water=3:1:6, putting them into a rice cooker, and cooking in standard mode for 30 min.

The hepatoprotective rice cooked by rice cooker for consumption alone is tested for composition and the results are shown in Table 2.

TABLE 2

Test of Composition

| | | Example 1 | |
| --- | --- | --- | --- |
| | Item | hepatoprotective rice | hepatoprotective rice (cooked) |
| 1 | Protein | 14.4 g/100 g | 8.6 g/100 g |
| 2 | Total sugar | 3.7 g/100 g | 2.8 g/100 g |
| 3 | Fat | 5.9 g/100 g | 2.0 g/100 g |
| 4 | Moisture | 9.1 g/100 g | 46.7 g/100 g |
| 5 | Iron | 31.8 mg/100 g | 22.7 mg/100 g |
| 6 | Potassium | 23.1 mg/100 g | 18.2 mg/100 g |
| 7 | Magnesium | 16 mg/100 g | 15 mg/100 g |
| 8 | Manganese | 0.61 mg/100 g | 0.52 mg/100 g |
| 9 | Zinc | 0.99 mg/100 g | 0.82 mg/100 g |
| 10 | Lead | N.D. (<0.05) | N.D. (<0.05) |
| 11 | Ash | 1.8 g/100 g | 1.1 g/100 g |
| 12 | Dietary fiber | 1.75 g/100 g | 1.14 g/100 g |

TABLE 2-continued

Test of Composition

| | | Example 1 | |
| --- | --- | --- | --- |
| | Item | hepatoprotective rice | hepatoprotective rice (cooked) |
| 13 | Total Carbohydrate | 63.35 g/100 g | 37.69 g/100 g |
| 14 | Total flavone | 0.24 g/100 g | 0.24 g/100 g |
| 15 | Procyanidine | 0.16 g/100 g | 0.030 g/100 g |
| 16 | Aflatoxin B1 | ug/kg (N.D. <5) | ug/kg (N.D. <5) |
| 17 | Benzex | ug/kg (N.D. <0.6) | ug/kg (N.D. <0.6) |
| 18 | DDT | ug/kg (N.D. <1.0) | ug/kg (N.D. <1.0) |
| 19 | Heptachlor | ug/kg (N.D. <0.8) | ug/kg (N.D. <0.8) |
| 20 | DDVP | mg/kg (N.D. <0.005) | mg/kg (N.D. <0.005) |
| 21 | Methamidophos | mg/kg (N.D. <0.006) | mg/kg (N.D. <0.006) |

In the cooked product, the ingredients in the kudzu root extract, corn oligopeptide, purple sweet potato powder and hawthorn extract are effectively retained, wherein anthocyanin has the function of preventing hypertension, alleviating liver dysfunction and the like, as well as an efficient anti-cancer function. Protein, Dietary fiber and trace element and the like ensure abundant nutritional value. The corn oligopeptide has excellent thermal stability and cool storage stability. Although both the stability is not reflected in Table 2, it is sure that no loss of stability is brought about by cooking. The cooked product has several aspects of effects such as alcoholism relief, anti-oxidation and hepatoprotection, and can be either eaten after drinking for alcoholism relief, or cooked in combination with ordinary rice for long-term consumption as daily staples.

Example 2

| Unit of measurement: | kg |
| --- | --- |
| Coarse rice powder | 80 |
| Isolated soy protein | 10 |
| Kudzu root extract | 0.01 |
| Corn oligopeptide | 5 |
| Purple sweet potato powder | 3 |
| Hawthorn extract | 2 |

The particular preparation method of the example comprises the steps of:

a. weighing each component according to the required amount of formulation, mixing uniformly coarse rice powder, isolated soy protein, kudzu root extract, corn oligopeptide, purple sweet potato powder with hawthorn extract to obtain the staring material A for use;

b. employing a double screw extruder to conduct texturized forming on the staring material A under high temperature and high pressure to obtain the product B, wherein the control parameters of production process include: feed rate of 250 kg/h, extrusion temperature of 120° C., water addition to moisture content of 18% and peeling speed of 480 rpm;

c. processing the product B under water-controlling by cold-blast air followed by the further steps of drying, dedusting and packaging, etc. to obtain the final product C.

TABLE 3

Test of Composition

| | Item | Example 2 | |
|---|---|---|---|
| 1 | Protein | hepatoprotective rice | hepatoprotective rice (cooked) |
| 2 | Total sugar | 14.4 g/100 g | 8.9 g/100 g |
| 3 | Fat | 3.7 g/100 g | 2.8 g/100 g |
| 4 | Moisture | 5.9 g/100 g | 2.0 g/100 g |
| 5 | Iron | 9.1 g/100 g | 47.2 g/100 g |
| 6 | Potassium | 23.2 mg/100 g | 18.2 mg/100 g |
| 7 | Magnesium | 16 mg/100 g | 14 mg/100 g |
| 8 | manganese | 0.61 mg/100 g | 0.55 mg/100 g |
| 9 | Zinc | 0.80 mg/100 g | 0.72 mg/100 g |
| 10 | Lead | N.D. (<0.05) | N.D. (<0.05) |
| 11 | Ash | 0.018 mg/100 g | N.D. (<0.01) |
| 12 | Dietary fiber | 1.8 g/100 g | 1.2 g/100 g |
| 13 | Total Carbohydrate | 1.75 g/100 g | 1.20 g/100 g |
| 14 | Total flavone | 63.35 g/100 g | 36.98 g/100 g |
| 15 | Lovastatin | 0.24 g/100 g | 0.23 g/100 g |
| 16 | Procyanidine | 8.01 mg/100 g | 4.77 mg/100 g |
| 17 | Aflatoxin B1 | 0.16 g/100 g | 0.020 g/100 g |

Items 18-21 corresponding to Table 1 are not detected.

Example 3

| Unit of measurement: | kg |
|---|---|
| Coarse rice powder | 75 |
| Isolated soy protein | 5 |
| Kudzu root extract | 1 |
| Corn oligopeptide | 0.5 |
| Purple sweet potato powder | 10 |
| Hawthorn extract | 9 |

The invention provides a method for producing a functional engineered rice which has dealcoholic and hepatoprotective functions and which is capable of enhancing the metabolism of ethanol inside the body, reducing liver damage and restoring liver vitality, the method comprising the steps of:

a. weighing each component according to the required amount of formulation, mixing uniformly coarse rice powder, isolated soy protein, kudzu root extract, corn oligopeptide, purple sweet potato powder with hawthorn extract to obtain the staring material A for use;

b. employing a double screw extruder to conduct texturized forming on the staring material A under high temperature and high pressure to obtain the product B, wherein the control parameters of production process include: feed rate of 280 kg/h, extrusion temperature of 140° C., water addition to moisture content of 25% and peeling speed of 520 rpm;

c. processing the product B under water-controlling by cold-blast air followed by the further steps of drying, dedusting and packaging, etc. to obtain the final product C.

TABLE 4

Test of Composition

| | Item | Example 3 | |
|---|---|---|---|
| 1 | Protein | hepatoprotective rice | hepatoprotective rice (cooked) |
| 2 | Total sugar | 14.4 g/100 g | 8.6 g/100 g |
| 3 | Fat | 3.7 g/100 g | 2.7 g/100 g |
| 4 | Moisture | 5.9 g/100 g | 2.0 g/100 g |
| 5 | Iron | 9.1 g/100 g | 46.9 g/100 g |
| 6 | Potassium | 26.3 mg/100 g | 20.2 mg/100 g |
| 7 | Magnesium | 16 mg/100 g | 15 mg/100 g |
| 8 | manganese | 0.61 mg/100 g | 0.39 mg/100 g |
| 9 | Zinc | 0.99 mg/100 g | 0.81 mg/100 g |
| 10 | Lead | N.D. (<0.05) | N.D. (<0.05) |
| 11 | Ash | 0.018 mg/100 g | N.D. (<0.01) |
| 12 | Dietary fiber | 1.8 g/100 g | 1.3 g/100 g |
| 13 | Total Carbohydrate | 1.75 g/100 g | 1.20 g/100 g |
| 14 | Total flavone | 63.35 g/100 g | 36.57 g/100 g |
| 15 | Lovastatin | 0.24 g/100 g | 0.24 g/100 g |
| 16 | Procyanidine | 8.01 mg/100 g | 4.73 mg/100 g |
| 17 | Aflatoxin B1 | 0.15 g/100 g | 0.019 g/100 g |

Items 18-21 corresponding to Table 1 are not detected.

Example 4

| unit of measurement: | kg |
|---|---|
| coarse rice powder | 85 |
| isolated soy protein | 6.5 |
| kudzu root extract | 5 |
| corn oligopeptide | 0.5 |
| purple sweet potato powder | 2 |
| hawthorn extract | 1 |

The invention provides a method for producing a functional engineered rice which has dealcoholic and hepatoprotective functions and which is capable of enhancing the metabolism of ethanol inside the body, reducing liver damage and restoring liver vitality, the method comprising the steps of:

a. weighing each component according to the required amount of formulation, mixing uniformly coarse rice powder, isolated soy protein, kudzu root extract, corn oligopeptide, purple sweet potato powder with hawthorn extract to obtain the staring material A for use;

b. employing a double screw extruder to conduct texturized forming on the staring material A under high temperature and high pressure to obtain the product B, wherein the control parameters of production process include: feed rate of 300 kg/h, extrusion temperature of 190° C., water addition to moisture content of 34% and peeling speed of 650 rpm;

c. processing the product B under water-controlling by cold-blast air followed by the further steps of drying, dedusting and packaging, etc. to obtain the final product C.

TABLE 5

Test of Composition

| | Item | Example 4 | |
|---|---|---|---|
| 1 | Protein | hepatoprotective rice | hepatoprotective rice (cooked) |
| 2 | Total sugar | 15.2 g/100 g | 9.1 g/100 g |
| 3 | Fat | 3.7 g/100 g | 2.9 g/100 g |
| 4 | Moisture | 5.7 g/100 g | 2.0 g/100 g |
| 5 | Iron | 9.1 g/100 g | 45.9 g/100 g |
| 6 | Potassium | 24.2 mg/100 g | 19.2 mg/100 g |
| 7 | Magnesium | 16 mg/100 g | 15 mg/100 g |
| 8 | manganese | 0.66 mg/100 g | 0.49 mg/100 g |
| 9 | Zinc | 0.89 mg/100 g | 0.72 mg/100 g |
| 10 | Lead | N.D. (<0.05) | N.D. (<0.05) |

TABLE 5-continued

Test of Composition

| Item | | Example 4 | |
|---|---|---|---|
| 11 | Ash | 0.020 mg/100 g | N.D. (<0.01) |
| 12 | Dietary fiber | 1.8 g/100 g | 1.3 g/100 g |
| 13 | Total Carbohydrate | 1.79 g/100 g | 1.25 g/100 g |
| 14 | Total flavone | 63.32 g/100 g | 36.56 g/100 g |
| 15 | Lovastatin | 0.24 g/100 g | 0.23 g/100 g |
| 16 | Procyanidine | 8.01 mg/100 g | 4.72 mg/100 g |
| 17 | Aflatoxin B1 | 0.15 g/100 g | 0.013 g/100 g |

Items 18-21 corresponding to Table 1 are not detected.

INDUSTRIAL APPLICABILITY

The present invention provides a functional engineered rice having dealcoholic and hepatoprotective functions for those drinking alcohol over an extended period of time or drinking alcohol excessively, and preparation method thereof. The engineered rice comprises six starting materials: coarse rice powder, isolated soy protein, kudzu root extract, corn oligopeptide, purple sweet potato powder, and hawthorn extract, and is prepared by: premixing the starting materials; employing a double screw extruder to conduct texturized processing and forming under high temperature and high pressure; and then drying, dedusting and packaging. The coarse cereal components of the engineered rice have the effects of balancing the diet and ensuring nutrition ingestion for those consuming the rice; and the functional factors such as the corn oligopeptide, the kudzu root extract and the like have the functions of enhancing ethanol metabolism inside the body, reducing liver damage, relieving alcoholism and protecting the liver.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An reconstituted rice having alcoholism relief and liver protection functions, comprising a reconstituted rice wherein the materials thereof comprise the following components by parts of weight: about 70-85% of coarse rice powder, about 5-25% of isolated soy protein, about 0.01-5% kudzu root extract wherein the kudzu root extract has an active ingredient including a puerarin content ≥40%, about 0.5-5% of corn oligopeptide including active ingredients, about 2-10% of purple sweet potato powder including active ingredients, about 1-9% of hawthorn extract wherein the hawthorn extract has an active ingredient including a hawthorn flavone content of 9% (measured by UV); the reconstituted rice includes a protein content of 14.4 g/100 g, a total sugar content of 3.7 g/100 g, a total fat content of 5.9 g/100 g, an iron content of 31.8 mg/100 g, a potassium content of 23.1 mg/100 g, a magnesium content of 16 mg/100 g, a manganese content of 0.61 mg/100 g, a zinc content of 0.99 mg/100 g, an ash content of 1.8 g/100 g, a dietary fiber content of 1.75 g/100 g, a total carbohydrate content of 63.35 mg/100 g, a total flavone content of 0.24 g/100 g, and a procyanidine content of 0.16 g/100 g, and wherein after the reconstituted rice is cooked, the active ingredients in the kudzu root extract, corn oligopeptide, purple sweet potato powder and hawthorn extract are effectively retained in the cooked product by at least 8.6 g/100 g of the protein content, at least 2.8 g/100 g of total sugar content, at least 2.0 g/100 g of fat content, at least 22.7 mg/100 g of iron content, at least 18.2 mg/100 g of potassium content, at least 15 mg/100 g of magnesium content, at least 0.52 mg/100 g of manganese content, at least 0.82 mg/100 g of zinc content, at least 1.1 g/100 g of ash content, at least 1.14 g/100 g of dietary fiber content, at least 37.69 g/100 g of total carbohydrate content, at least 0.24 g/100 g of total flavone content, and at least 0.030 g/100 g of procyanidine content.

2. A method for preparing the reconstituted rice having alcoholism relief and liver protection functions according to claim 1, comprising the steps of:
a. weighing each component according to the required amount of formulation, mixing uniformly coarse rice powder, isolated soy protein, kudzu root extract, corn oligopeptide, purple sweet potato powder with hawthorn extract to obtain the staring material A for use;
b. employing a double screw extruder to conduct extrusion forming to obtain the product B, wherein the control parameters of production process are: feed rate of 200-300 kg/h, extrusion temperature of 80-190° C., moisture content of 10-34% and peeling speed of 400-650 rpm;
c. processing the product B under water-controlling by cold-blast air followed by the steps of drying, dedusting and packaging to obtain the final product C.

3. A method for preparing the reconstituted rice for ingestion according to claim 1 wherein the reconstituted rice can be steamed or cooked in a rice cooker by itself or with ordinary rice in accordance with the ratios of:
a. reconstituted rice:water=1:0.7, after water boils then transfer to steam bowl, and steam for 15 minutes; or
b. reconstituted rice:water=1:1.4, add both to rice cooker and cook in ultra-fast mode for 20 minutes; or
c. ordinary rice:reconstituted rice:water=3:1:4, after water boils put all components into steam bowl, and steam for 40 minutes; or
d. ordinary rice:reconstituted rice:water=3:1:6, add all components to rice cooker, and cook in standard mode for 30 minutes.

4. A method of relieving alcoholism and increasing liver protection functions for metabolizing ethanol, comprising:
Preparing an reconstituted rice comprising the following components by parts of weight: about 70-85% of coarse rice powder, about 5-25% of isolated soy protein, about 0.01-5% kudzu root extract, about 0.5-5% of corn oligopeptide, about 2-10% of purple sweet potato powder, about 1-9% of hawthorn extract; and
Ingesting the reconstituted rice along with ethanol.

5. The reconstituted rice of claim 1, wherein the active ingredients of the purple sweet potato power comprises proteins, 18 types of amino acids digested and absorbed by human body, 8 vitamins comprising vitamin C, B and A, and more than 10 natural minerals comprising phosphorus, iron, selenium, and anthocyanin.

* * * * *